(12) United States Patent
Horie et al.

(10) Patent No.: US 7,927,308 B2
(45) Date of Patent: Apr. 19, 2011

(54) PUNCTURE DEVICE

(75) Inventors: Osamu Horie, Osaka (JP); Hiromichi Komori, Yokohama (JP); Hirotaka Haro, Chuo (JP)

(73) Assignee: Medtronic Sofamor Danek, Co., Ltd., Osaka-Shi (JP)

( * ) Notice: Subject to any disclaimer, the term of this patent is extended or adjusted under 35 U.S.C. 154(b) by 116 days.

(21) Appl. No.: 12/446,551

(22) PCT Filed: Nov. 28, 2007

(86) PCT No.: PCT/JP2007/072980
§ 371 (c)(1),
(2), (4) Date: May 11, 2009

(87) PCT Pub. No.: WO2008/078499
PCT Pub. Date: Jul. 3, 2008

(65) Prior Publication Data
US 2010/0305517 A1    Dec. 2, 2010

(30) Foreign Application Priority Data
Nov. 27, 2006  (JP) ................. 2006-351309

(51) Int. Cl.
*A61M 5/178* (2006.01)
(52) U.S. Cl. ................ 604/164.01; 604/164.13
(58) Field of Classification Search ............ 604/164.01, 604/164.13, 264
See application file for complete search history.

(56) References Cited

U.S. PATENT DOCUMENTS

| 6,231,546 | B1 | 5/2001 | Milo et al. |
| 2002/0019626 | A1 | 2/2002 | Sharkey et al. |
| 2006/0167437 | A1 | 7/2006 | Valencia |

FOREIGN PATENT DOCUMENTS

| JP | 2002-508987 A | 3/2002 |
| JP | 2003-523258 A | 8/2003 |
| JP | 2006-527629 A | 12/2006 |

*Primary Examiner* — Tatyana Zalukaeva
*Assistant Examiner* — Deanna K Hall
(74) *Attorney, Agent, or Firm* — Birch, Stewart, Kolasch & Birch, LLP (57) ABSTRACT

A puncture device that reliably acts on the target body site is proposed. The puncture device includes a luminal puncture body 2 having a projection opening 2a on the side surface; a tube 3, accommodated in the puncture body 2, having an acting part 3a that acts on the inside of the body; and a leading means 4 for projecting the acting part 3a of the tube 3 towards the side from the projection opening 2a. The leading means 4 includes a wire 5 inserted in the tube 3, and a moving means 6 for moving the wire 5 in the length direction of the puncture body 2, the moving means 6 adjusting the moving amount of the wire 5 to project the wire 5 from the projection opening 2a. The acting part 3a of the tube 3 can be projected by the projection of the wire 5.

6 Claims, 10 Drawing Sheets

PUNCTURE DEVICE

TECHNICAL FIELD

The present invention relates to a puncture device for injecting medicinal agent or irradiating laser to the target site in the body, or taking in internal substance from the target location.

BACKGROUND ART

Figure 13:
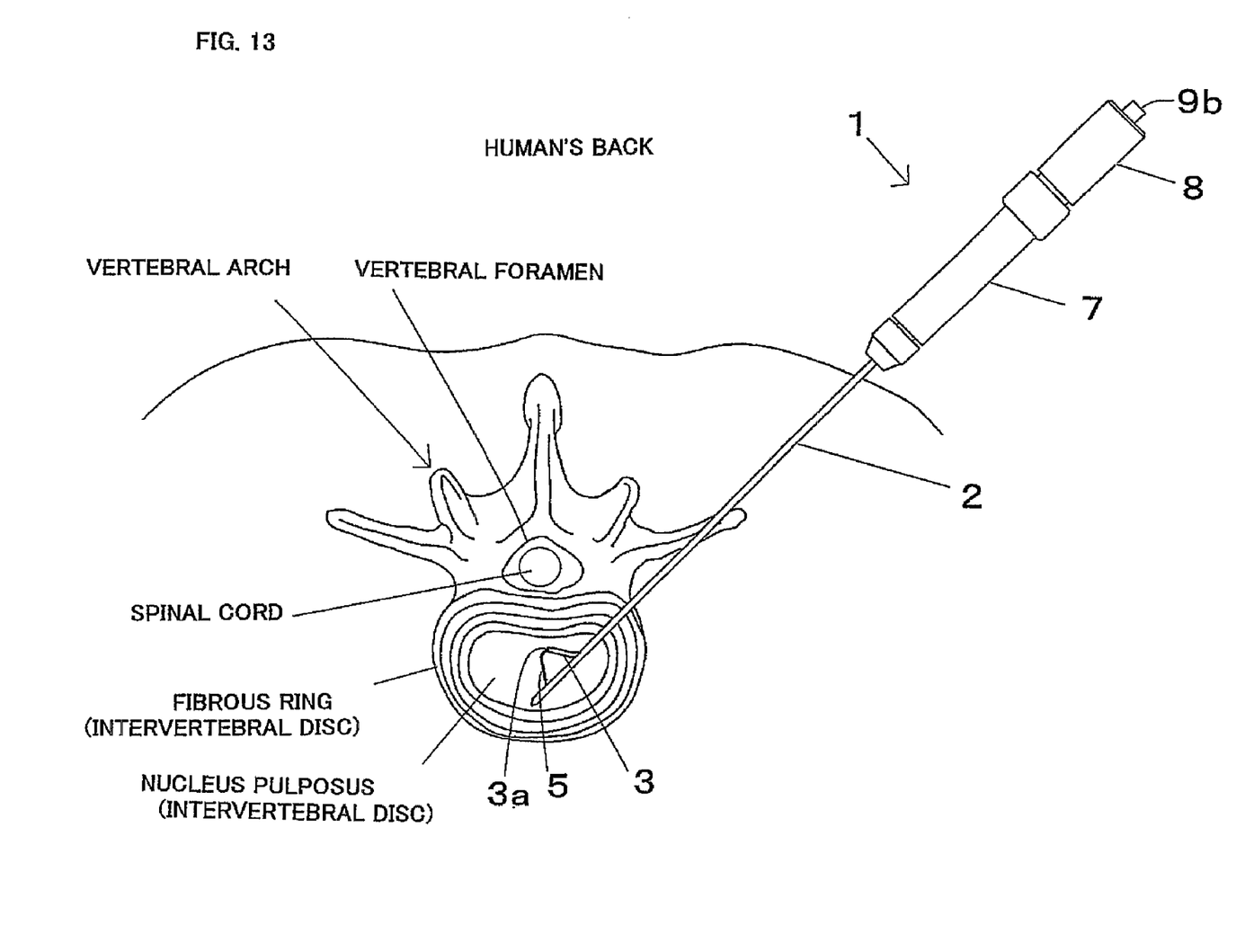
FIG. 13 is a view showing the usage state of the puncture device of the present embodiment.

The spine is formed with 24 vertebrae overlapping one over the other in the vertical direction, and the vertebrae are connected by the intervertebral disc. As shown in FIG. 13, the intervertebral disc is a circular disc shaped cartilage having fibrous ring surrounding the nucleus pulposus of jelly form at the center, and has a function of alleviating the impact. The vertebra is made up of the vertebral body and the vertebral arch of the back, and vertebral foramen is formed between the vertebral arches. The spinal cord runs through the vertebral foramen.

Disk herniation occurs at the spine such as the cervical vertebra, lumbar vertebra, etc. and may be a state (exuding type) in which cracks form in the fibrous ring, and nucleus pulposus therein exudes out therefrom, and a state (bulging type) in which cracks do not form in the fibrous ring and nucleus pulposus and the fibrous ring bulge out together, where symptoms such as severe pain, swelling, etc. occur since the spinal cord and the nerve root on the back side are compressed by the exuded (bulged out) nucleus pulposus.

Treatment includes conservative treatment and operation, where operation is performed if not curable with the conservative treatment. The operation includes Love method of extracting the hernia, vertebral body fixing method, intervertebral disc enzyme injection treatment of injecting enzyme into the intervertebral disc through puncture method to reduce the internal pressure and depressurizing the nerve root under compressive stimulation, percutaneous nucleus pulposus extracting method of partially removing the nucleus pulposus similar to intervertebral disc contrast by external approach without using medicine to reduce the internal pressure of the intervertebral disc, etc.

Among them, the medicinal agent must be accurately injected to the affected area when treating with medicinal agent such as in intervertebral disc enzyme injection treatment. Accuracy is also desired when injecting contrast agent. Normally, the needle is punctured using a puncture tool, and medicinal agent, etc. is injected from the opening at the distal end of the needle when injecting medicine or contrast agent.

However, the direction of puncturing the needle is limited to a constant direction diagonally from the back side due to positional relationship of spinal cord and internal organs, bone, etc. in the operation (FIG. 13). Therefore, the medicinal agent, etc. can be injected only in the puncturing direction of the needle (inserting direction of the needle), whereby the medicinal agent is injected to the entire intervertebral disc and the medicinal agent acts on areas other than the affected area. Conventionally, the medicinal agent thus cannot be injected in a direction different from the puncture direction and it is difficult to exclusively act the medicinal agent on the affected area.

Patent document 1 discloses a device to be inserted into the intervertebral disc in order to perform a certain function inside the intervertebral disc, and a method of the same. This device includes a catheter with a lumen, and a guide wire having a distal end and a proximal end configured so as to be positioned inside the lumen of the catheter and to move with respect to the lumen, the guide wire guiding itself towards the selected portion of the intervertebral disc inside the internal portion of the intervertebral disc, and the catheter moving forward with respect to the guide wire so as to follow the path of the guide wire up to the selected portion inside the internal portion of the intervertebral disc.

[Patent document 1] Japanese Laid-Open Patent Publication No. 2003-523258

DISCLOSURE OF THE INVENTION

Problems to be Solved by the Invention

However, the device disclosed in patent document 1 cannot forcibly direct the mouth of the catheter to the direction different from the puncturing direction since the guide wire is extended from the distal end of the catheter. Furthermore, the guide wire only moves forward along the inner wall of the fibrous ring, and the movement thereof cannot be controlled, which makes it difficult to lead the catheter to the target location.

In view of the above problems, the present invention aims to provide a puncture device that reliably acts on the target location.

Means to Solve the Problems

In order to achieve the above aim, the present invention proposes a puncture device including a luminal puncture body having a projection opening on the side surface; an acting body accommodated in the puncture body and having an acting part acting on the inside of the body; and a leading means for projecting the acting part of the acting body towards the side from the projection opening.

The acting part can be directed to a direction different from the puncture direction since the acting part can be projected towards the side from the projection opening formed at the side surface of the puncture body. Therefore, the device is suitably used particularly in cases where the puncture direction is limited due to arrangement of nerves, bones, internal organs, etc. such as when performing operation for disc herniation. The directivity is high since the acting part can be directed in the opening direction of the projection opening.

The number of projection openings needs to be at least one and may be in plurals. The position formed with the projection opening is preferably at the distal end side of the puncture body, but is not limited thereto.

The acting part is a part that provides some action on the inside of the body, and may be an injection port for injecting substances such as medicinal agent, contrast agent, implant, etc.; intake port for removing internal substances; electrical acting point of heat, light, laser, etc.; lens and the like of the imaging device, but is not limited thereto. The acting body can be changed according to the purpose such as tube (catheter) for injecting the substance into the body or taking in the substance of the body; a member for providing electrical action such as laser irradiation, etc.; imaging device, etc. The position where the acting part is formed may be at the distal end or at the side surface of the acting body.

Regarding the leading means, the acting body itself may be made of shape memory material, and the acting part may be projected from the projection opening at a predetermined condition; or the acting body may be supported with other materials such as wire, and the acting part may be projected from the projection opening. In the latter case, other materials such as wire is made of shape memory material, and the acting part is projected from the projection opening at a predetermined condition, but the leading means may be configured by a wire, accommodated in the puncture body, for leading the acting body, and a moving means for moving the wire in and out towards the side of the puncture body from the projection opening. The acting part can be projected or accommodated with the moving in and out of the wire from the projection opening.

The moving means moves the wire with respect to the puncture body in a length direction. When the wire is moved towards the distal end side of the puncture body, the wire deflects in the puncture body, and one part thereof projects out from the projection opening. With the projection of the wire, the acting part supported at the wire projects out from the projection opening. On the contrary, when the wire is moved towards the proximal side of the puncture body, the deflection of the wire in the puncture body is removed, thereby returning the wire to a linear form. The acting part can be accommodated in the puncture body with the movement of the wire. The operation of projecting and accommodating the acting part is thus performed with a simple configuration. The vicinity of the distal end of the wire is fixed to the puncture body or is contacted to a stopper to produce deflection in the wire.

More specifically, the moving means is configured by an operation part that freely axially rotates with respect to the puncture body, and a wire supporting part screw fit and coupled to the operation part and having its axial rotation regulated, the wire supporting part and the wire supported by the wire supporting part being moved with respect to the puncture body in the length direction by axially rotating the operation part.

Another configuration of the moving means includes screw fitting and coupling the operation part so as to be movable forward and backward with respect to the puncture body in the length direction, and supporting the wire in a freely axial rotating manner. The deflection is produced in the wire in the puncture body when the operation part is moved towards the distal end side, whereby the acting part projects out from the projection opening. The wire does not need to be axially rotated since the wire is supported in a freely axial rotating manner by the operation part.

Yet another configuration of the moving means includes deflecting the wire portion and restoring the wire to linear shape by operating a piston type lever, or deflecting the wire portion and restoring the wire portion to linear shape by pushing and pulling the operation part in a piston form similar to a syringe.

The moving means can adjust the projecting amount of the acting part. Since the moving amount of the wire, the projecting amount of the wire and the projecting amount of the acting part are proportional with each other, the projecting amount of the acting part can be adjusted by adjusting the moving distance of the wire with the moving means.

Furthermore, the moving means can change the orientation of the acting part. The operation of higher accuracy thus becomes possible with such configuration.

The support of the acting body by the wire may be performed by fixing the wire to the acting body through adhesion, tightening, etc., but if the acting body has a tubular shape, the wire is inserted and supported in the tube. The wire is preferably inserted into the tube as the movement of the wire is accurately transmitted to the acting body when inserted into the tube.

Effect of the Invention

According to the present invention, the acting part can be directed to a direction different from the puncture direction since the acting part can be projected towards the side from the projection opening formed at the side surface of the puncture body. Therefore, the device is suitably used particularly in cases where the puncture direction is limited due to arrangement of nerves, bones, internal organs, etc. such as when performing operation for disc herniation.

BRIEF DESCRIPTION OF THE DRAWINGS

FIG. 11 is a cross sectional view of a puncture device of the present embodiment, where (a) is a cross sectional side view showing a projected state of the acting part, (b) is a cross sectional side view showing an accommodated state of the acting part;
FIG. 12 is an enlarged cross sectional view of the main parts of the puncture device of the present embodiment, where (a) is a cross sectional side view showing a projected state of the acting part, (b) is a cross sectional front view showing an accommodated state of the acting part.

DESCRIPTION OF SYMBOLS 1 puncture device
2 puncture body
2a projection opening
3 tube
3a acting part
4 leading means
5 wire
6 moving means
7 handle part
8 operation part
9 wire supporting part
10 nut

DETAILED DESCRIPTION OF THE PREFERRED EMBODIMENTS

Figure 1:
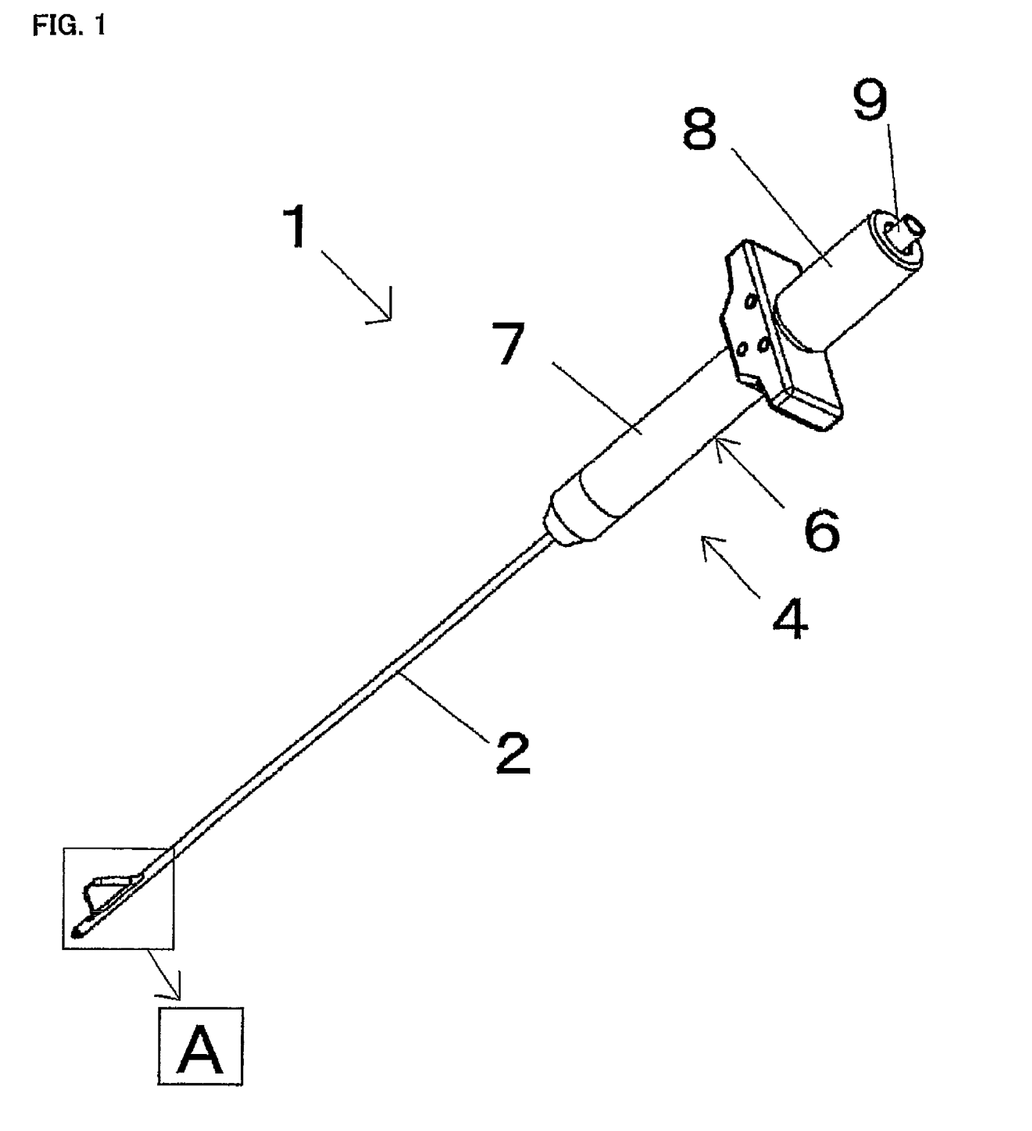
FIG. 1 is a perspective view of a puncture device of the present embodiment, showing a projected state of the acting part.
Figure 2:
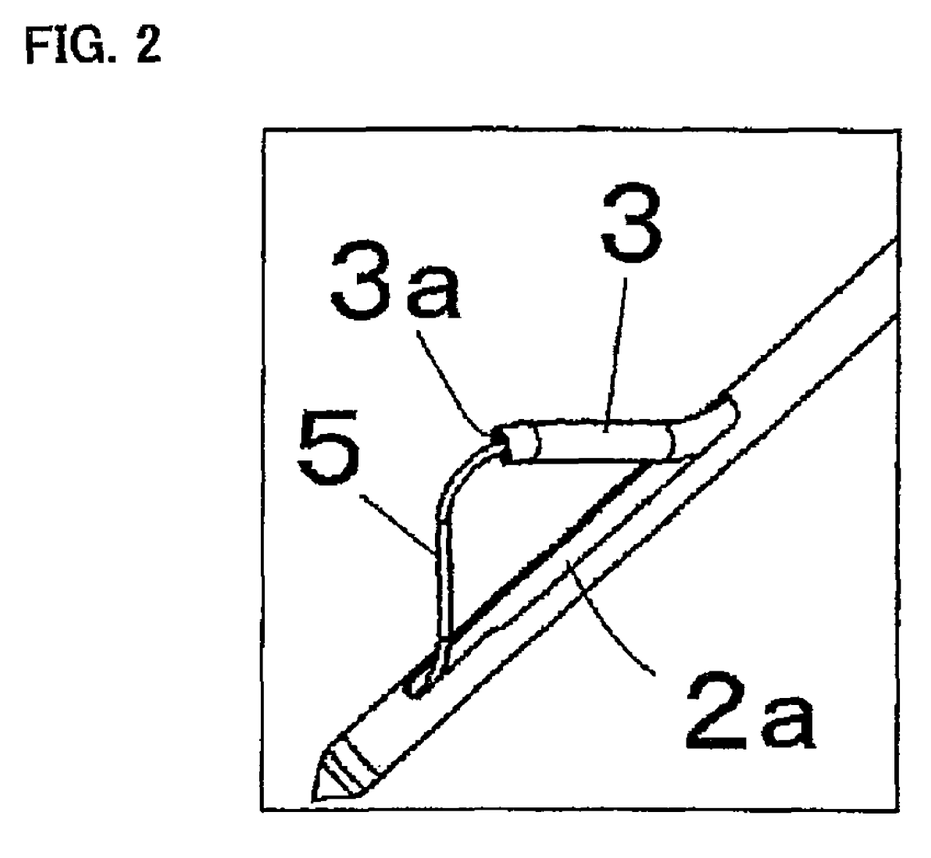
FIG. 2 is an enlarged view of "A" in FIG. 1.
Figure 3:
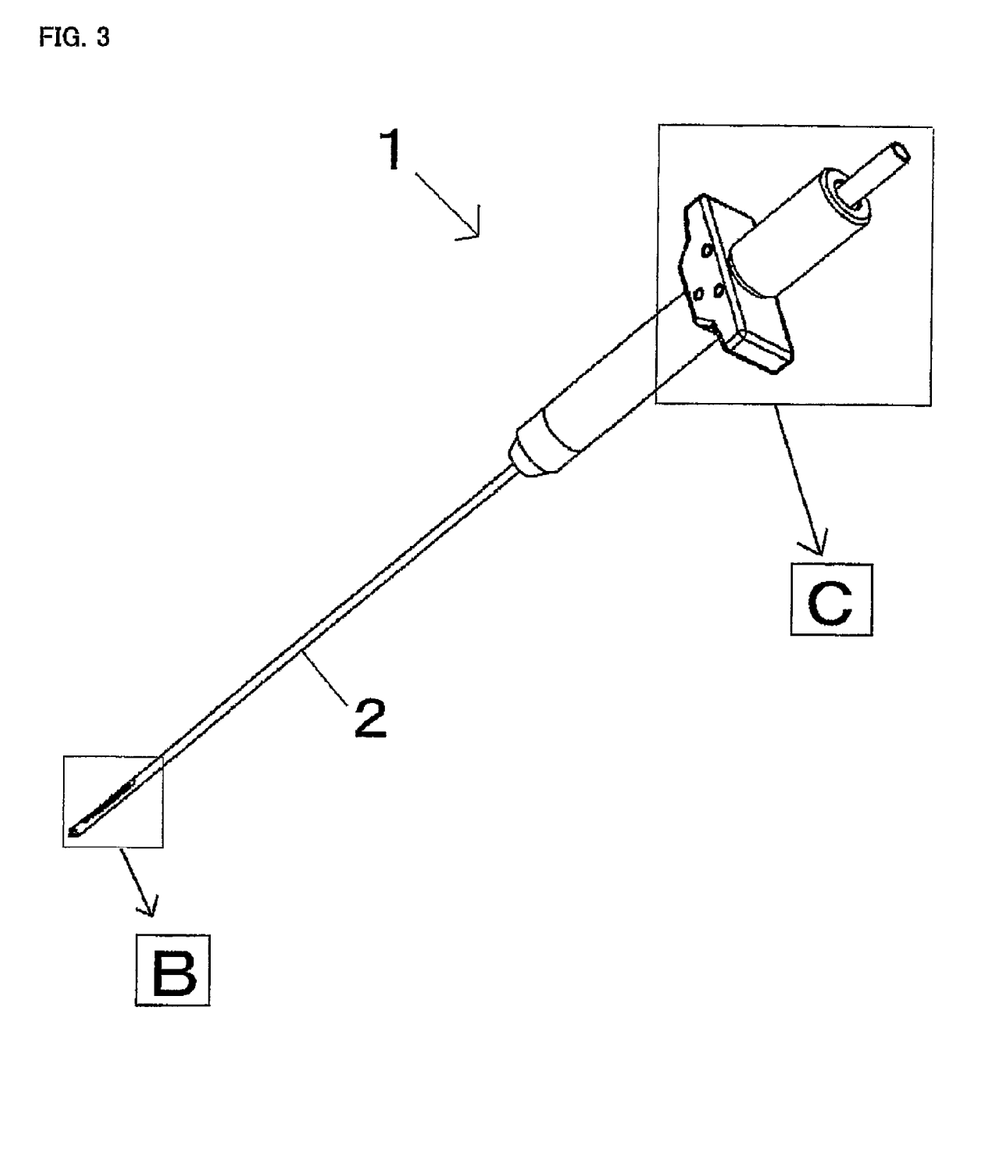
FIG. 3 is a perspective view of a puncture device of the present embodiment, showing an accommodated state of the acting part.
Figure 4:
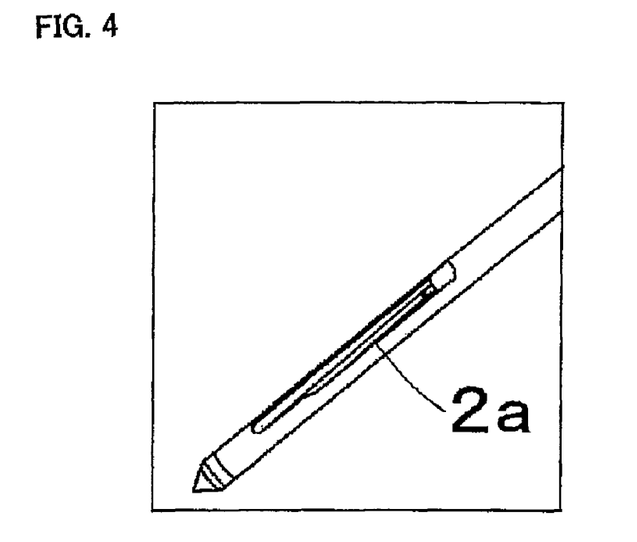
FIG. 4 is an enlarged view of "B" in FIG. 3.
Figure 5:
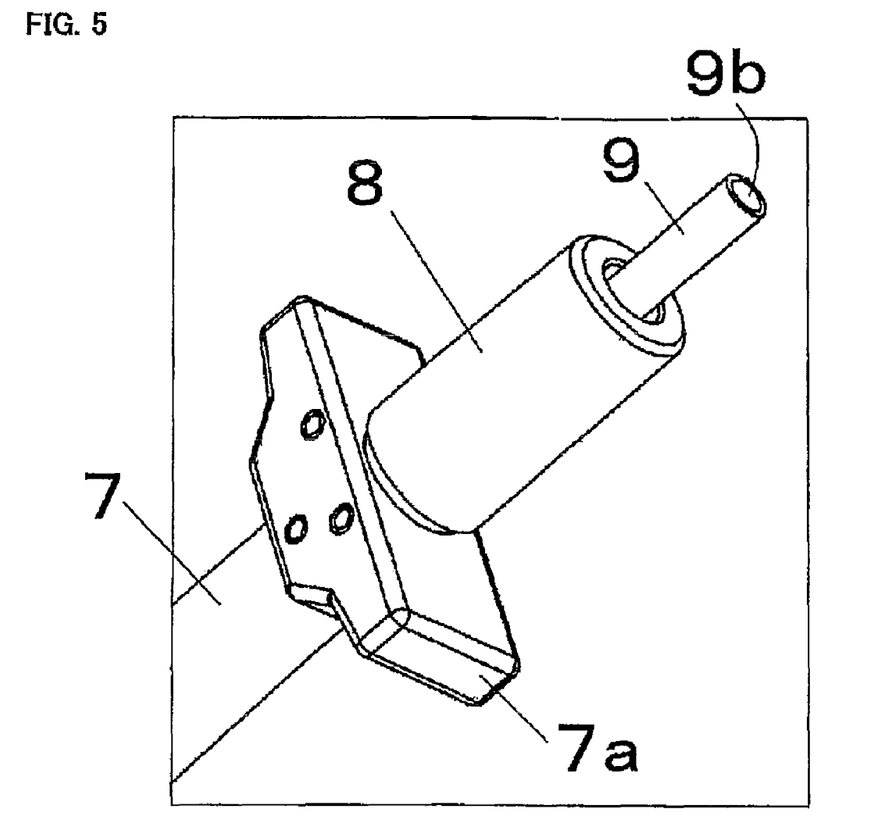
FIG. 5 is an enlarged view of "C" in FIG. 3.
Figure 6:
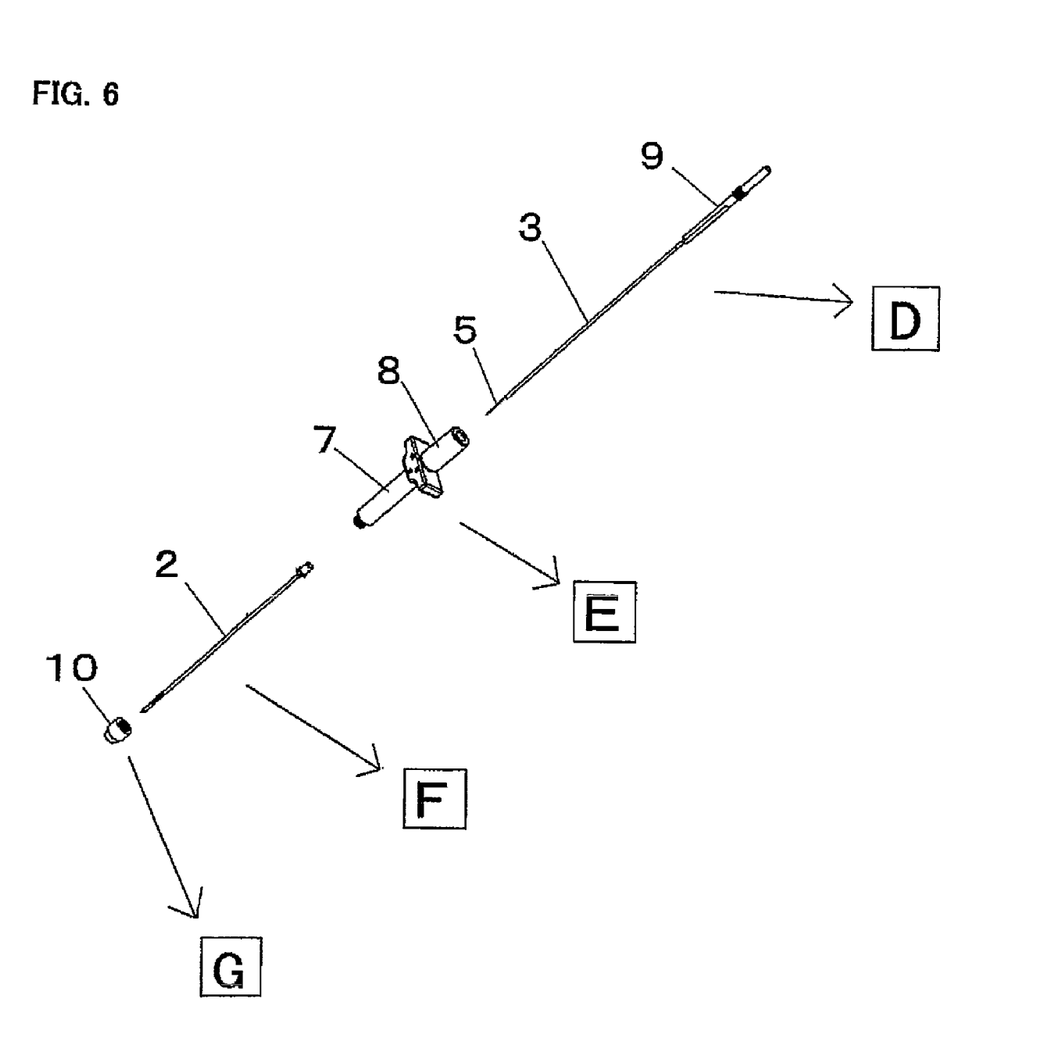
FIG. 6 is an exploded perspective view of a puncture device of the present embodiment.
Figure 7:
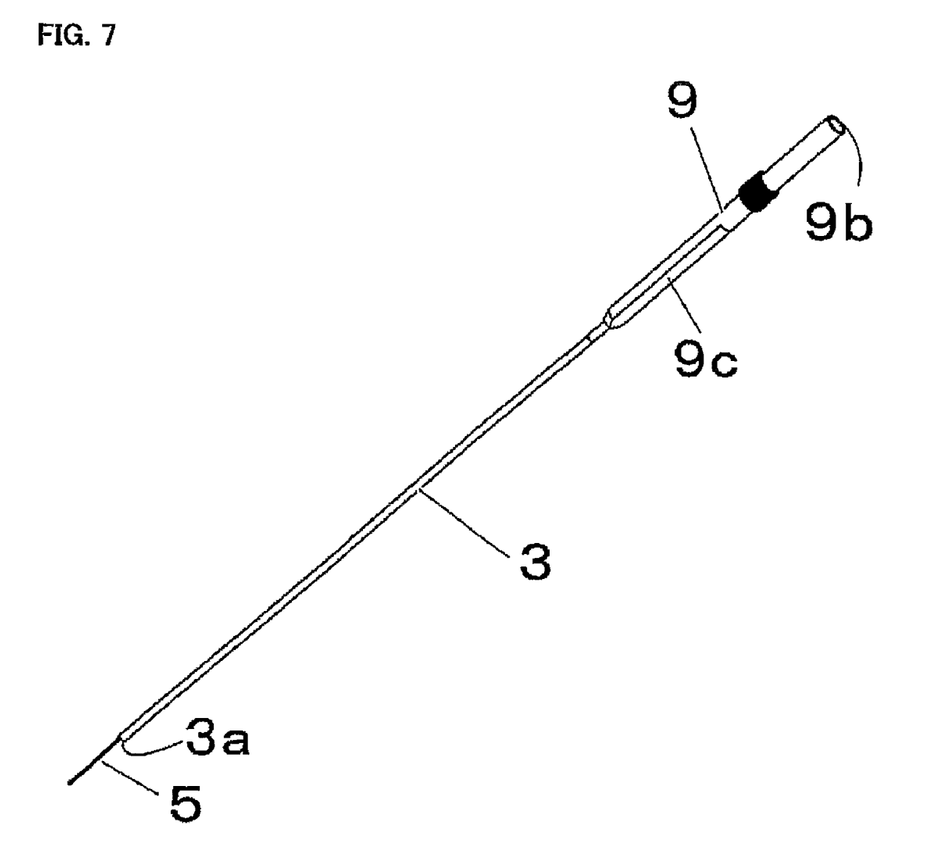
FIG. 7 is an enlarged view of "D" in FIG. 6.
Figure 8:
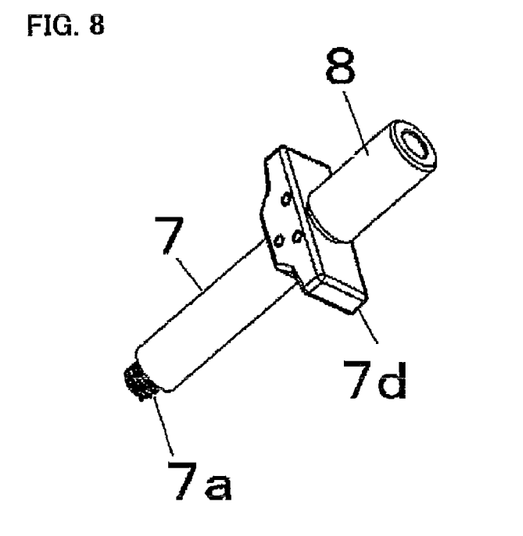
FIG. 8 is an enlarged view of "E" in FIG. 6.
Figure 9:
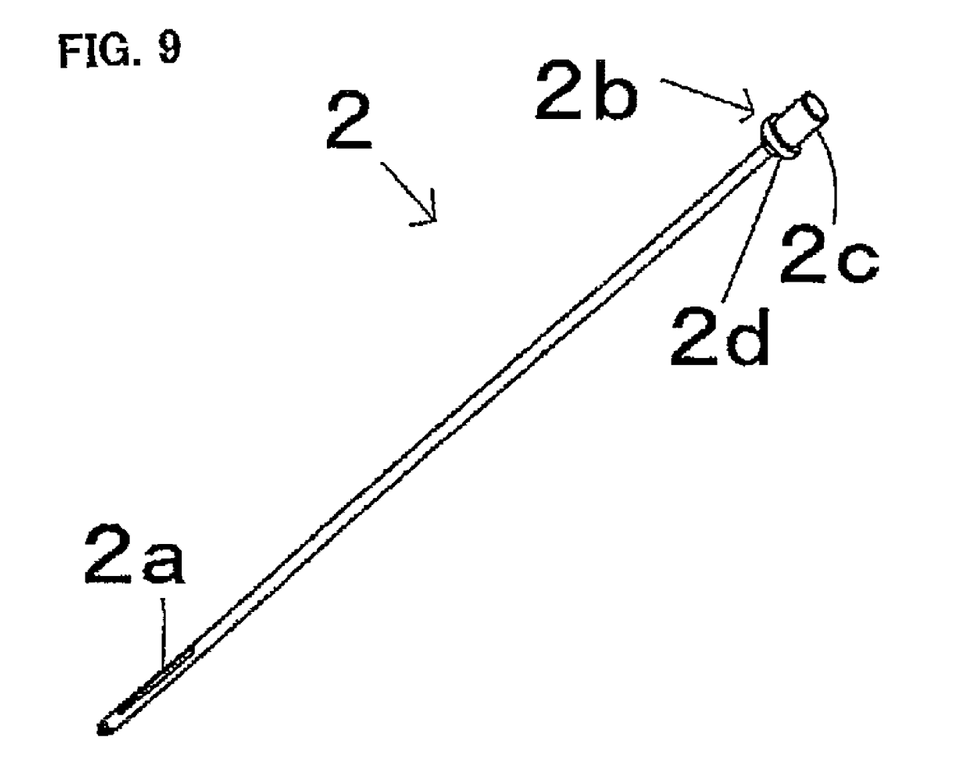
FIG. 9 is an enlarged view of "F" in FIG. 6.
Figure 10:
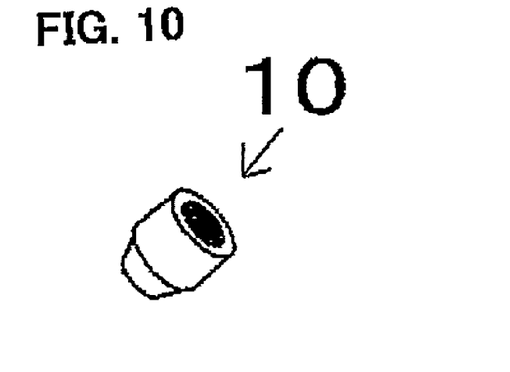
FIG. 10 is an enlarged view of "G" in FIG. 6.
Figure 11:
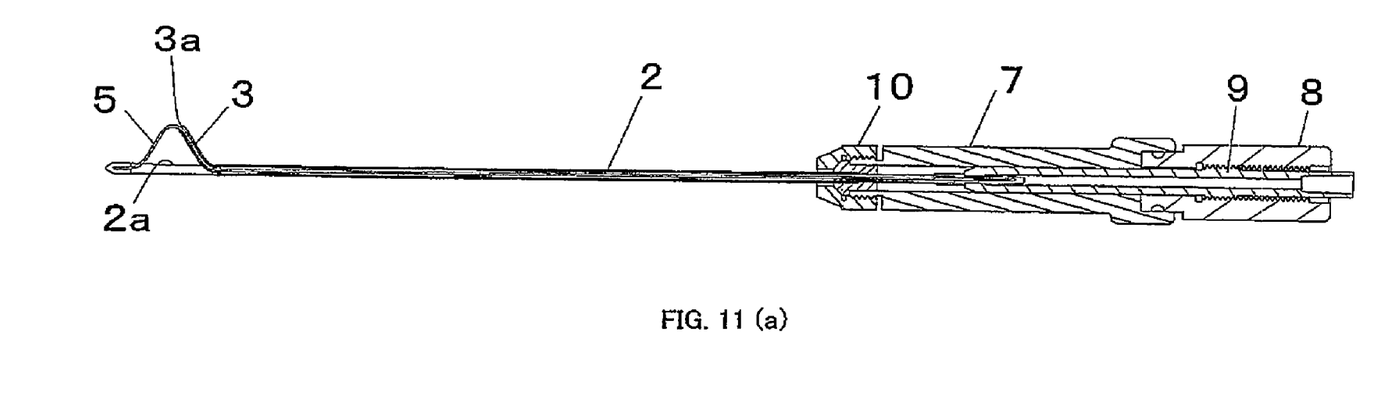
Figure 11B:
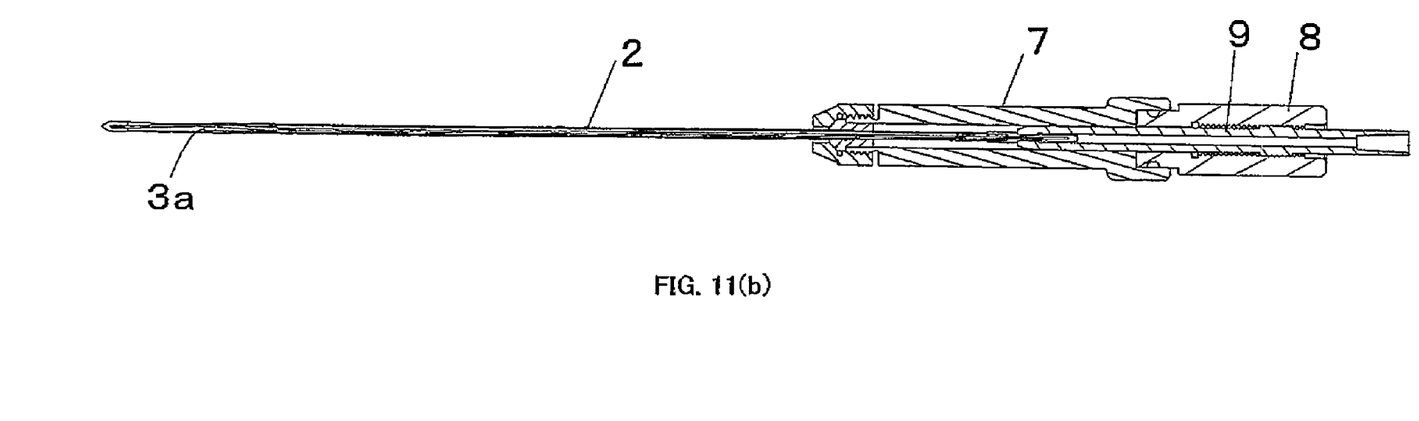
Figure 12A:
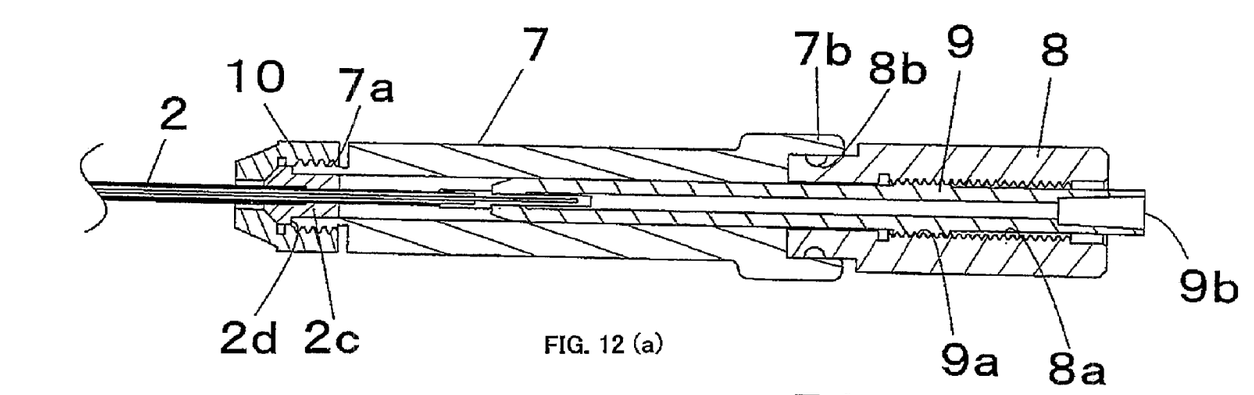
Figure 12B:
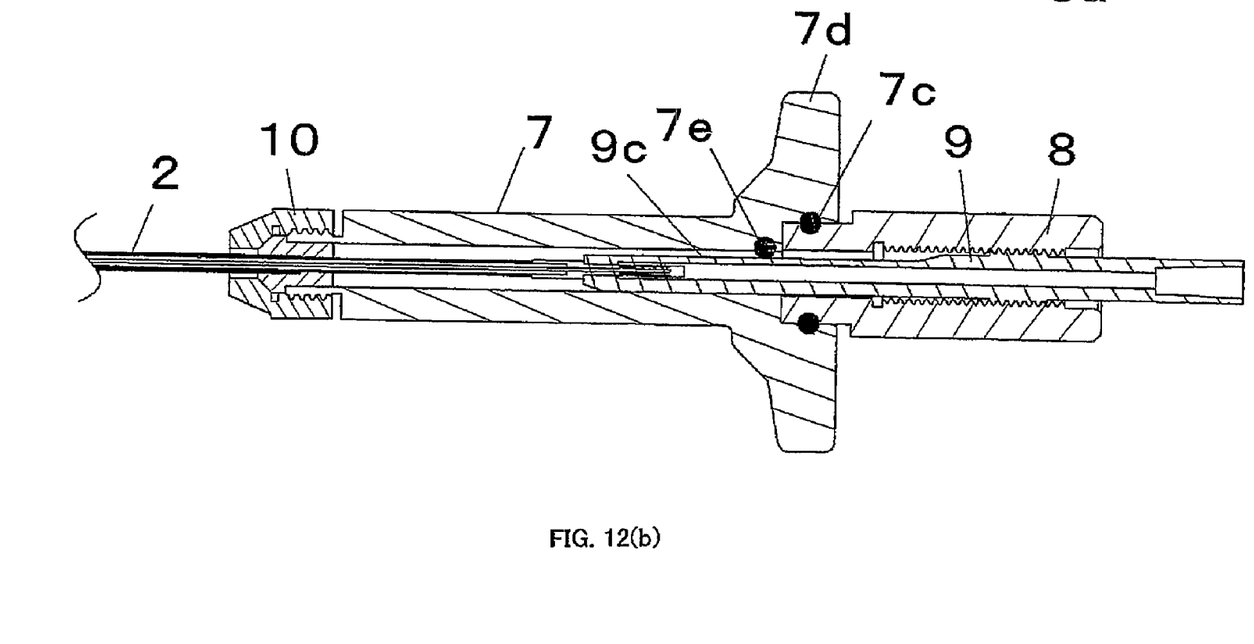

The embodiment of the present invention will now be described based on the figures. FIG. 1 is a perspective view of a puncture device of the present embodiment, showing a projected state of the acting part; FIG. 2 is an enlarged view of "A" in FIG. 1; FIG. 3 is a perspective view of a puncture device of the present embodiment, showing an accommodated state of the acting part; FIG. 4 is an enlarged view of "B" in FIG. 3; FIG. 5 is an enlarged view of "C" in FIG. 3; FIG. 6 is an exploded perspective view of a puncture device of the present embodiment; FIG. 7 is an enlarged view of "D" in FIG. 6; FIG. 8 is an enlarged view of "E" in FIG. 6; FIG. 9 is an enlarged view of "F" in FIG. 6; FIG. 10 is an enlarged view of "G" in FIG. 6; FIG. 11 is a cross sectional view of a puncture device of the present embodiment, where (a) is a cross sectional side view showing a projected state of the acting part, (b) is a cross sectional side view showing an accommodated state of the acting part; FIG. 12 is an enlarged cross sectional view of the main parts of the puncture device of the present embodiment, where (a) is a cross sectional side view showing a projected state of the acting part, (b) is a cross sectional front view showing an accommodated state of the acting part; and FIG. 13 is a view showing the usage state of the puncture device of the present embodiment.

The puncture device 1 in the present embodiment includes a luminal puncture body 2 having a projection opening 2a on the side surface, a tube 3 serving as an acting body that is accommodated in the puncture body 2 and that has the acting part 3a that acts inside the body, and a leading means 4 for projecting the acting part 3a of the tube 3 from the projection opening 2a and leading the acting part 3a of the tube 3 in the predetermined direction, as shown in FIGS. 1-12. The leading means 4 includes a wire 5, accommodated in the puncture body 2, for leading the acting body, and a moving means 6 for freely moving in and out the wire 5 from the projection opening 2a.

The puncture body 2 is a tubular body made of stainless steel including a lumen part inside and the projection opening 2a on the side surface, where the distal end is formed into a tapered shape to be obstructed. The material of the puncture body 2 is not limited to the above and other materials such as nitinol may be used. The projection opening 2a is a longitudinal opening in the axial direction formed at the side surface on the distal end side of the puncture body 2. A connecting part 2b for connecting with a handle part 7, to be hereinafter described, is arranged at the opening end on the proximal side of the puncture body 2. The connecting part 2b is configured by an inserting portion 2c to be inserted into the handle part 7, and a stopper 2d.

The tube 3 is a resin tube of cylindrical shape, the opening on the distal end side of which becomes the acting part 3a. An opening that becomes the acting part 3a may be formed on the side part of the tube 3. The material of tube 3 may be changed to other materials such as rubber as long as the material has flexibility of a certain extent that can be projected from the projection opening 2a. The wire 5 is inserted into the tube 3, and the proximal end of the tube 3 is fixed to a wire supporting part 9, to be hereinafter described, along with the wire 5. The distal end (acting part 3a) of the tube 3 is arranged at a position facing the projection opening 2a.

The wire 5, made of nitinol and formed into a linear form, has the distal end thereof arranged at the position contacting the distal end of the puncture body 2, and is fixed to the internal surface of the puncture body 2. The material of the wire 5 merely needs to have a rigidity of an extent of leading the tube 3, and other metals such as stainless steel, etc., or other materials such as resin, etc. may be used. The shape of the wire 5 is not limited to linear shape, and may be formed into other shapes such as tape shape. Furthermore, a state in which the distal end of the wire 5 is not fixed to the puncture body 2, or a state in which the distal end of the wire 5 is moved away from the distal end of the puncture body 2 may be used. The wire 5 can be deflected since the distal end of the wire 5 contacts the distal end of the puncture body 2 when the wire 5 is moved towards the distal end side of the puncture body 2 by the moving means 6.

The moving means 6 includes the luminal handle part 7 fixed to the puncture body 2; a luminal operation part 8 supported in a freely axially rotating manner at the luminal part of the handle part 7 and formed with a screw portion 8a on the inner peripheral surface; and a wire supporting part 9 for supporting the wire 5, being accommodated in the handle part 7 and the operation part 8, and being formed with a screw portion 9a that screw fits the screw portion 8a of the operation part 8 on the outer peripheral surface. The handle part may be integrally formed with the puncture body.

The handle part 7 and the operation part 8 are made of metal or made of resin. The handle part 7 is formed with a screw portion 7a at the peripheral surface of the end on the distal end side, and after inserting the inserting portion 2c of the connecting part 2b of the puncture body 2 into the screw portion 7a, the inserting portion 2c is fixed by a nut 10, thereby connecting and fixing the handle part 7 and the puncture body 2. An enlarging part 7b having an inner diameter larger than the other part is formed into a step form at the end on the proximal side of the handle part 7, and the operation part 8 is fitted into the enlarged part 7b in a freely axially rotating manner. A groove 8b is formed in the peripheral direction at the outer peripheral surface of the operation part 8, and the handle part 7 regulates the movement in the axis direction of the operation part 8 by fitting a fixing pin 7c on the inner surface of the enlarging part 7b into the groove 8b. Furthermore, a gripping part 7d is formed at the outer peripheral surface of the end on the proximal side of the handle part 7 so as to have a substantially T-shape in side view. The handle part 7 is more easily gripped by the gripping part 7d.

The wire supporting part 9 is a cylindrical body, and fixes the proximal ends of the wire 5 and the tube 3. The wire supporting part 9 is accommodated in the handle part 7 and the operation part 8. A screw part 9a is formed on the peripheral surface of the wire supporting part 9, and is screw fit and coupled to the screw part 8a of the operation part 8. A groove 9c extending in the axial direction is formed on the outer peripheral surface of the wire supporting part 9, and the handle part 7 regulates the axis rotation of the wire supporting part 9 by fitting the fixing pin 7e on the outer surface of the handle part 7 into the groove 9c. The opening 9b on the proximal end of the wire supporting part 9 is communicated to the acting part 3a of the tube 3, whereby medicinal agent is inserted from the opening 9b of the wire supporting part 9 and discharged from the acting part 3a.

According to the above configuration, the movement in the axis direction of the operation part 8 is regulated, and the axial rotation of the wire supporting part 9 is regulated, whereby the wire supporting part 9 screw fit and coupled to the operation part 8 and the wire 5 can be moved in and out in the length direction with respect to the puncture body 2 by axially rotating the operation part 8 with respect to the handle part 7 (puncture body 2). That is, the deflected amount of the wire 5 can be adjusted through the rotating operation of the operation part 8 such that the wire 5 is deflected by moving the wire supporting part 9 towards the distal end side, and, to the contrary, the deflection of the wire 5 is removed by moving the wire supporting part 9 towards the proximal side. The deflected amount of the wire 5 is proportional to the projecting amount of the wire 5 from the projecting port 2a, that is, the projecting amount of the acting part 3a, and thus the projecting amount of the acting part 3a can be adjusted. Furthermore, since the wire projects from the projecting port 2a in a hill shape, the angle of inclined surface of the hill can be changed by the projecting amount of the wire 5, and the orientation of the acting part 3a can be changed.

A case of performing the operation of disc herniation using the puncture device 1 of the above configuration will now be briefly described with reference to FIG. 13. In the intervertebral disc enzyme injection treatment of injecting the medicinal agent such as enzyme into the intervertebral disc to reduce the internal pressure and depressurizing the nerve root under compressive stimulation, the portion of the puncture body 2 is first diagonally punctured from the back side of the patient with the tube 3 accommodated in the puncture body 2. The handle part 7 is then axially rotated to direct the orientation of the projecting port 2a towards the affected area side, and the operation part 8 is thereafter axially rotated to project the acting part 3a along with the wire 5. After adjusting the projecting amount of the wire 5 so that the acting part 3a is directed towards the affected area, the medicinal agent is inserted from the opening 9b, and the medicinal agent is discharged from the acting part 3a through the wire supporting part 9 and the tube 3. Therefore, the medicinal agent effectively acts on the affected area since the acting part 3a is directed towards the affected area.

It will be understood that the present invention is not limited to the above embodiment, and various modifications and changes may be made to the embodiment within the scope of the present invention. For example, a case of performing the operation for disc herniation has been described in the above embodiment, but the present invention may be applied to the operation for other body parts such as eye ball.

INDUSTRIAL APPLICABILITY

The present invention can be advantageously utilized for a puncture device that reliably acts on the target location.

What is claimed is:

1. A puncture device comprising a luminal puncture body having a projection opening on the side surface; an acting body accommodated in the puncture body and having an acting part acting on the inside of the body; and a leading means for projecting the acting part of the acting body towards the side from the projection opening,
   wherein the leading means includes a wire, accommodated in the puncture body, for leading the acting body, and a moving means for moving the wire in and out to the side of the puncture body from the projection opening,
   and wherein the distal end of the wire is fixed to the puncture body, and when the wire is moved so as to be deflected by the moving means with respect to the puncture body in a length direction, one part of the wire projects out from the projection opening thereby to project the acting part from the projection opening towards the side.

2. The puncture device according to claim 1, wherein the acting body is a tube, and the wire is inserted into the tube.

3. The puncture device according to claim 1, wherein the moving means includes an operation part that freely axially rotates with respect to the puncture body, and a wire supporting part screw fit and coupled to the operation part and having its axial rotation regulated, the wire being moved with respect to the puncture body in the length direction by axially rotating the operation part.

4. The puncture device according to claim 1, wherein the moving means adjusts the projecting amount of the acting part.

5. The puncture device according to claim 1, wherein the moving means changes the orientation of the acting part.

6. The puncture device according claim 1, wherein the puncture device is applied to the intervertebral disc.

* * * * *